US008747388B2

(12) United States Patent
Pandey et al.

(10) Patent No.: US 8,747,388 B2
(45) Date of Patent: Jun. 10, 2014

(54) ACCESS AND DRAINAGE DEVICES

(75) Inventors: Prabhakar Pandey, Cumberland, MD (US); David W. Robertson, Framingham, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 13/534,881

(22) Filed: Jun. 27, 2012

(65) Prior Publication Data

US 2012/0265020 A1    Oct. 18, 2012

Related U.S. Application Data

(63) Continuation of application No. 11/111,097, filed on Apr. 20, 2005, now abandoned.

(51) Int. Cl.
*A61M 27/00* (2006.01)
*A61B 1/32* (2006.01)
*A61M 25/00* (2006.01)

(52) U.S. Cl.
CPC ......... *A61M 27/008* (2013.01); *A61M 25/0017* (2013.01); *A61M 2210/1078* (2013.01); *A61M 2210/1082* (2013.01); *A61M 2210/1085* (2013.01); *A61M 2210/1089* (2013.01)
USPC .......... 604/544; 604/540; 604/48; 604/93.01; 604/94.01; 604/104; 604/105; 604/106; 604/317

(58) Field of Classification Search
CPC ............... A61M 27/008; A61M 2025/0037; A61M 25/0017; A61M 2025/0034; A61M 2210/1078; A61M 2210/1082; A61M 2210/1085; A61M 2210/1089
USPC .......... 604/540, 544, 48, 93.01, 94.01, 95.03, 604/104, 105, 106, 317
See application file for complete search history.

(56) References Cited

U.S. PATENT DOCUMENTS

| | | | | |
|---|---|---|---|---|
| 2,798,745 | A |   | 7/1957 | Nelson |
| 3,495,595 | A |   | 2/1970 | Soper |
| 3,970,090 | A | * | 7/1976 | Loiacono ................ 604/104 |
| 4,265,243 | A | * | 5/1981 | Taylor ................... 604/128 |
| 4,320,761 | A |   | 3/1982 | Haddad |
| 4,405,313 | A |   | 9/1983 | Sisley et al. |
| 4,425,124 | A | * | 1/1984 | Womack ................ 604/544 |
| 4,567,882 | A |   | 2/1986 | Heller |
| 4,670,009 | A |   | 6/1987 | Bullock |
| 4,671,795 | A |   | 6/1987 | Mulchin |
| 4,676,782 | A |   | 6/1987 | Yamamoto et al. |
| 4,701,159 | A |   | 10/1987 | Brown et al. |
| 4,893,621 | A | * | 1/1990 | Heyman ................. 606/127 |
| 5,041,083 | A |   | 8/1991 | Tsuchida et al. |
| 5,053,023 | A | * | 10/1991 | Martin ................... 604/523 |
| 5,096,454 | A |   | 3/1992 | Samples |

(Continued)

OTHER PUBLICATIONS

"Cook Ureteral Access Sheath", Cook Urological Inc., 2001, 1 page.

(Continued)

*Primary Examiner* — Adam Marcetich

(57) ABSTRACT

A medical device can be used to drain fluids from the body during a medical procedure that requires the insertion of a medical instrument into an anatomical lumen or cavity. The device generally allows the simultaneous introduction of the medical instrument into the body and drainage of fluid out of the body during a medical procedure.

19 Claims, 11 Drawing Sheets

(56) References Cited

U.S. PATENT DOCUMENTS

| | | | |
|---|---|---|---|
| 5,178,803 A | 1/1993 | Tsuchida et al. | |
| 5,190,520 A | 3/1993 | Fenton et al. | |
| 5,197,951 A * | 3/1993 | Mahurkar | 604/43 |
| 5,221,256 A | 6/1993 | Mahurkar | |
| 5,224,931 A | 7/1993 | Kumar | |
| 5,318,517 A | 6/1994 | Reiman | |
| 5,374,245 A | 12/1994 | Mahurkar | |
| 5,380,304 A | 1/1995 | Parker | |
| 5,405,341 A | 4/1995 | Martin | |
| 5,421,824 A | 6/1995 | Clement et al. | |
| 5,514,112 A | 5/1996 | Chu et al. | |
| 5,569,182 A | 10/1996 | Twardowski et al. | |
| 5,571,093 A | 11/1996 | Cruz et al. | |
| 5,571,161 A | 11/1996 | Starksen | |
| 5,578,018 A | 11/1996 | Rowland et al. | |
| 5,637,091 A | 6/1997 | Hakky et al. | |
| 5,685,867 A | 11/1997 | Twardowski et al. | |
| 5,700,253 A | 12/1997 | Parker | |
| 5,746,713 A | 5/1998 | Hood et al. | |
| 5,947,953 A * | 9/1999 | Ash et al. | 604/508 |
| 5,954,652 A | 9/1999 | Heyman | |
| 5,957,928 A | 9/1999 | Kirwan, Jr. | |
| 5,997,547 A | 12/1999 | Nakao et al. | |
| 6,063,119 A | 5/2000 | Pintauro et al. | |
| 6,183,413 B1 | 2/2001 | Migachyov | |
| 6,402,736 B1 * | 6/2002 | Brown et al. | 604/523 |
| 6,524,268 B2 | 2/2003 | Hayner et al. | |
| 6,572,612 B2 | 6/2003 | Stewart et al. | |
| 6,673,040 B1 | 1/2004 | Samson et al. | |
| 6,695,832 B2 | 2/2004 | Schon et al. | |
| 6,699,216 B2 | 3/2004 | Ikeguchi | |
| 6,733,536 B1 | 5/2004 | Gellman | |
| 6,739,341 B2 | 5/2004 | Tihon et al. | |
| 6,764,519 B2 | 7/2004 | Whitmore, III | |
| 6,849,068 B1 | 2/2005 | Bagaoisan et al. | |
| 6,921,378 B2 | 7/2005 | O'Keefe et al. | |
| 6,929,626 B2 | 8/2005 | DiCarlo et al. | |
| 6,929,664 B2 | 8/2005 | Kolb | |
| 8,057,424 B2 | 11/2011 | Patterson et al. | |
| 2002/0038115 A1 | 3/2002 | Dulak et al. | |
| 2002/0045868 A1 * | 4/2002 | Reever | 604/328 |
| 2002/0188167 A1 | 12/2002 | Viole et al. | |
| 2002/0188246 A1 | 12/2002 | Hayner et al. | |
| 2003/0109837 A1 | 6/2003 | McBride-Sakal | |
| 2005/0107736 A1 * | 5/2005 | Landman et al. | 604/93.01 |
| 2005/0125072 A1 | 6/2005 | Kolb | |
| 2005/0148999 A1 * | 7/2005 | Beaufore et al. | 604/544 |
| 2005/0197624 A1 * | 9/2005 | Goodson et al. | 604/96.01 |
| 2006/0047269 A1 | 3/2006 | Reever et al. | |
| 2006/0058575 A1 | 3/2006 | Zaddem et al. | |
| 2007/0078438 A1 | 4/2007 | Okada | |

OTHER PUBLICATIONS

"Ureteral Access Sheath Set", Applied Medical, 2000, 2 pages.
International Search Report and Written Opinion for PCT/US06/13108, mailed Sep. 10, 2007, 9 pages.
International Preliminary Report on Patentability for PCT/US06/13108, mailed Nov. 1, 2007, 6 pages.
"Plastics Extrusion", from Wikipedia, the free encyclopedia, Dec. 4, 2009, 5 pages.

* cited by examiner

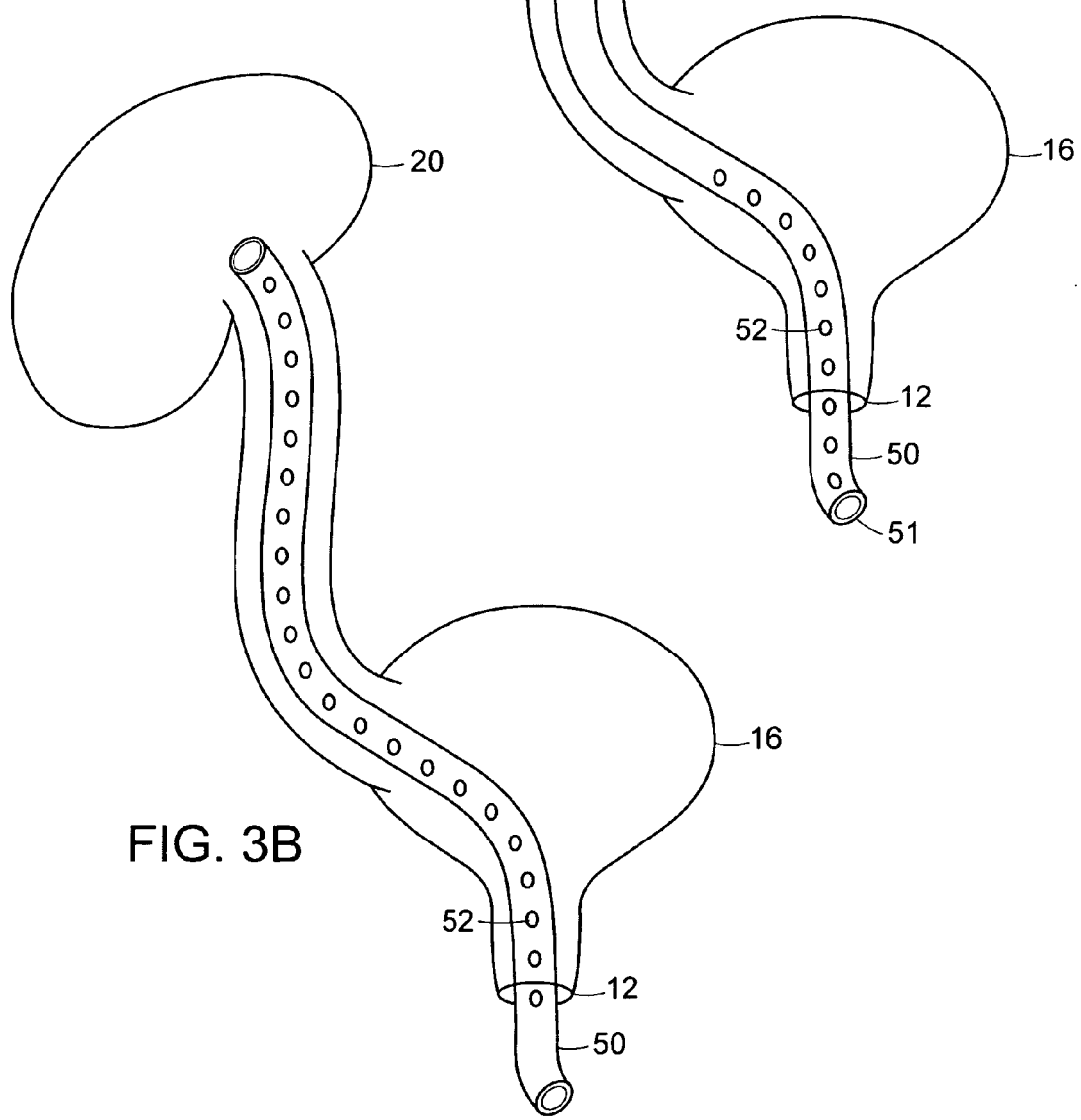

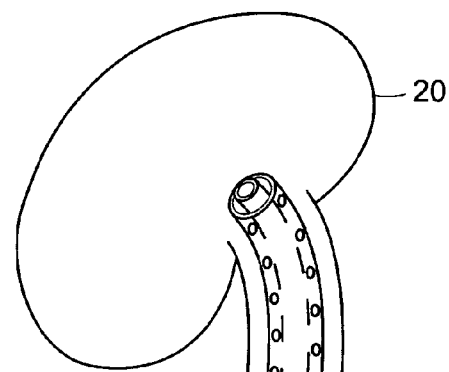
FIG. 4A
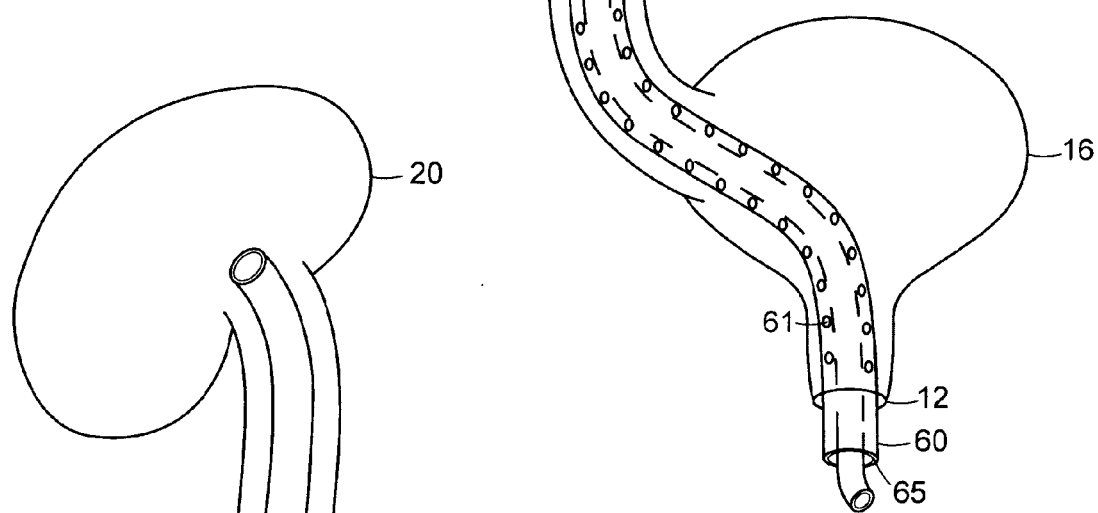
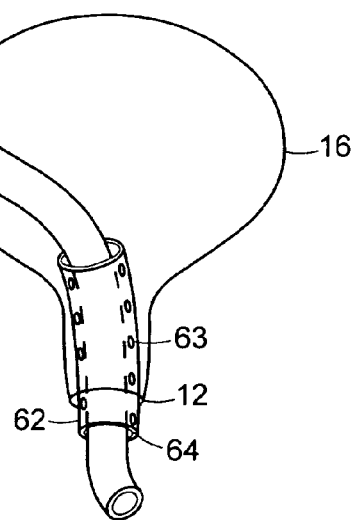
FIG. 4B

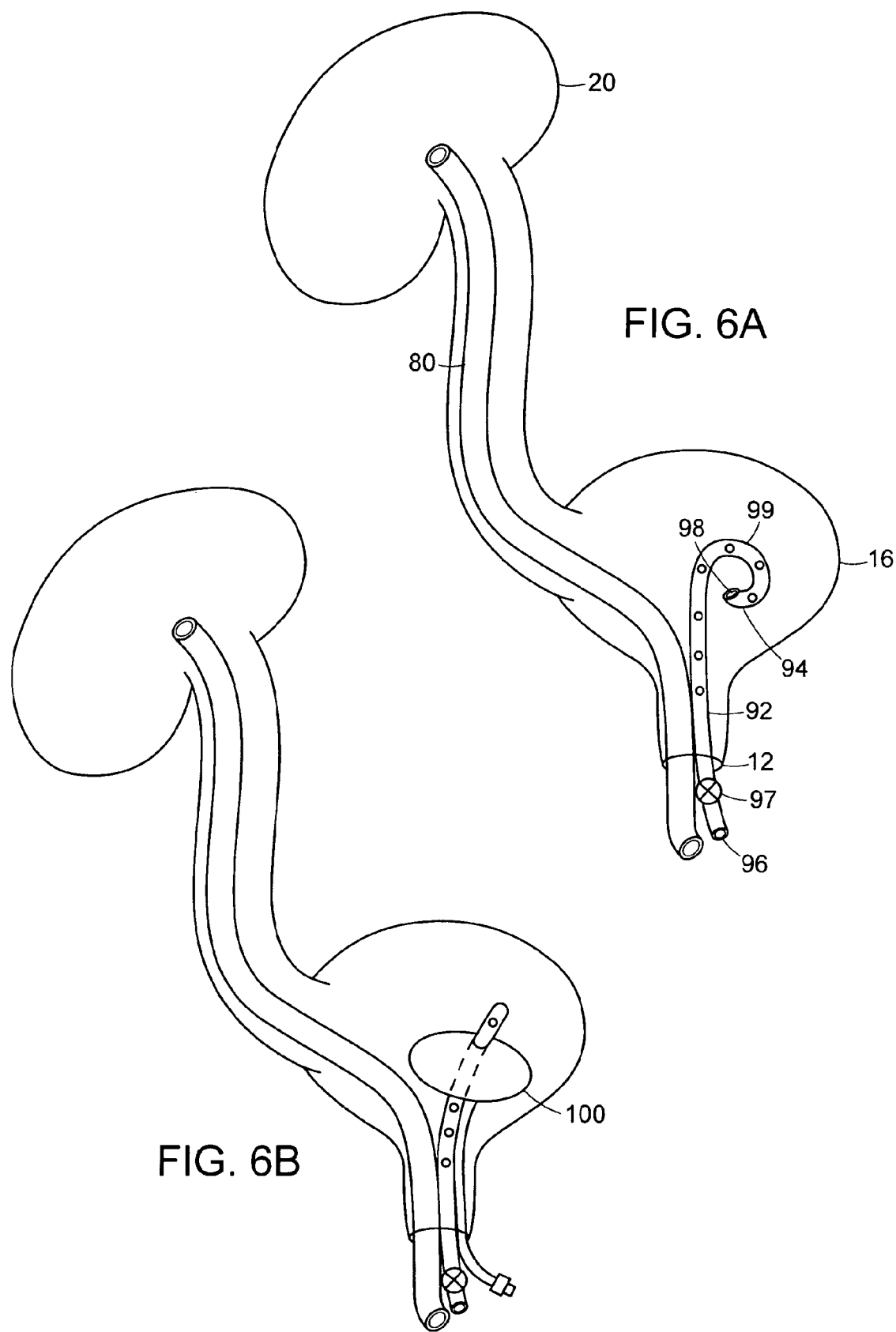

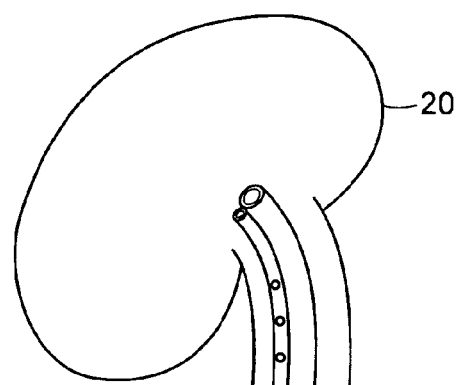
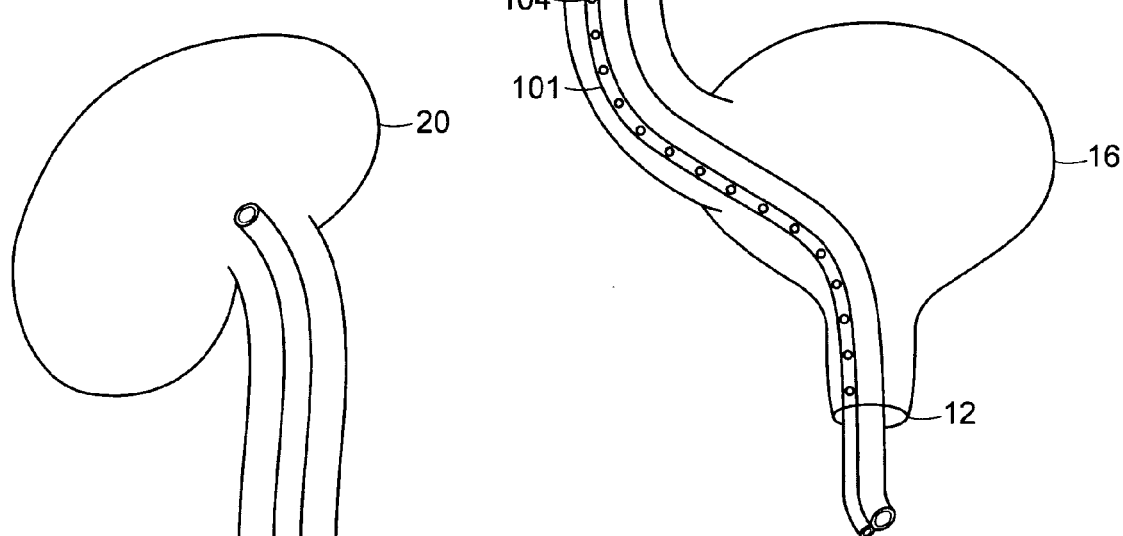
FIG. 7A
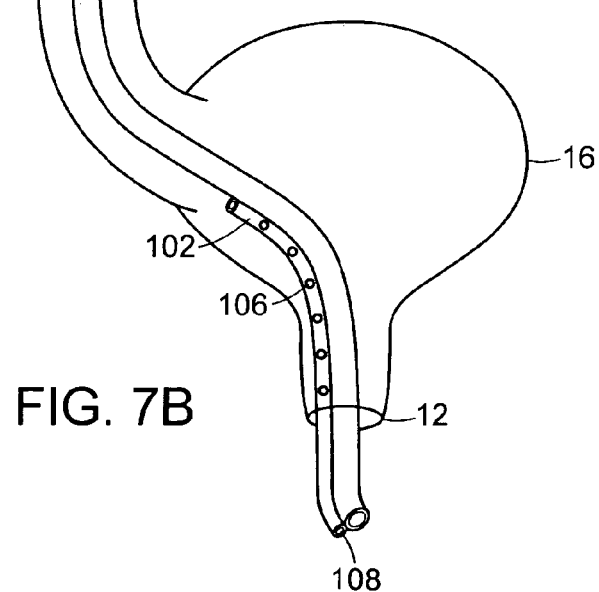
FIG. 7B

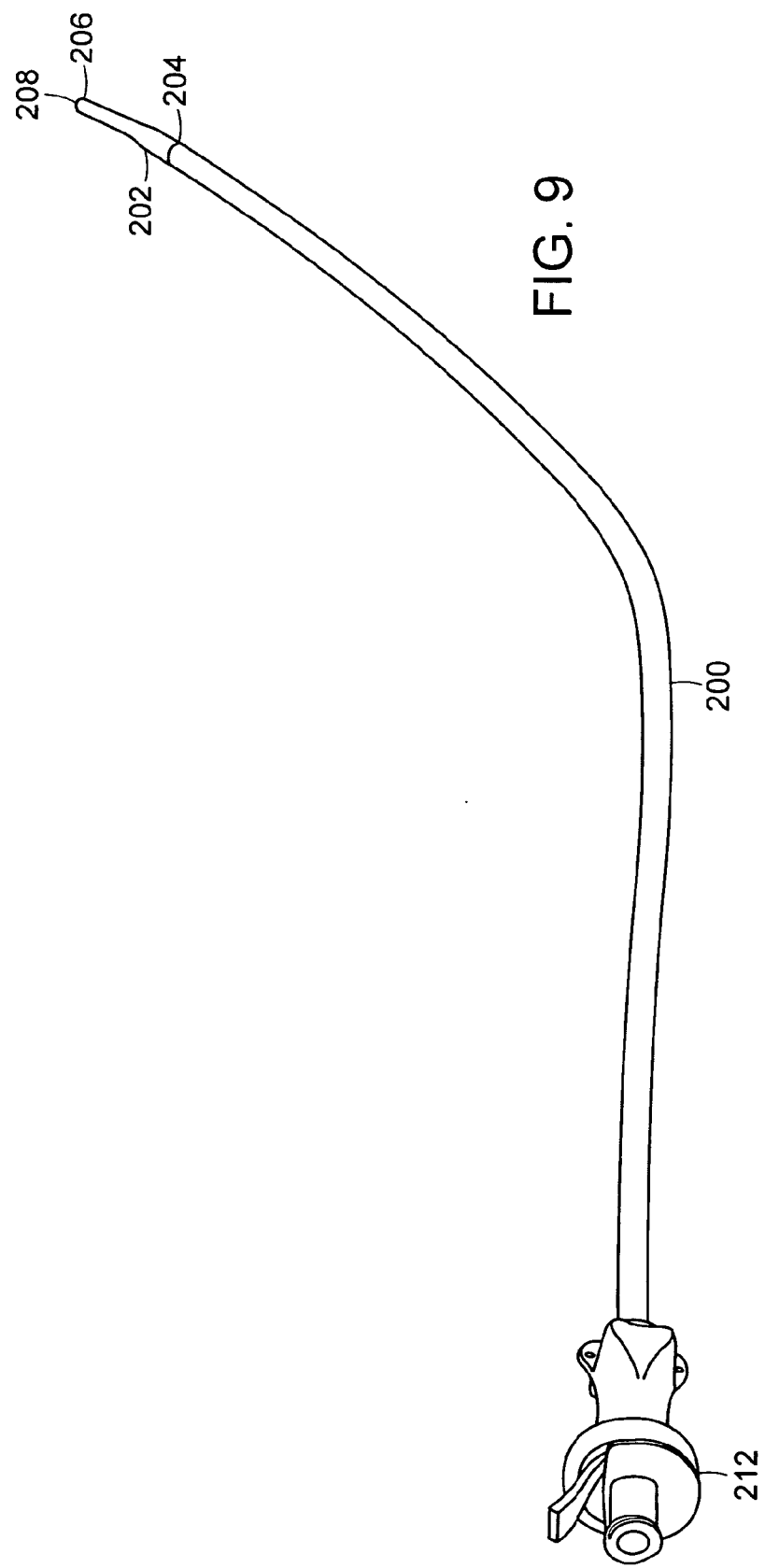

ACCESS AND DRAINAGE DEVICES

CROSS-REFERENCE TO RELATED APPLICATION

This application is a Continuation of, and claims priority to, U.S. patent application Ser. No. 11/111,097, filed Apr. 20, 2005, entitled "ACCESS AND DRAINAGE DEVICES AND METHODS OF USE THEREOF", which is incorporated by reference herein in its entirety.

TECHNICAL FIELD

The invention relates to ureteral devices. More specifically, the invention relates to ureteral access devices and methods of their use.

BACKGROUND

Medical evaluation and treatment involving the urinary tract of a patient often require medical instruments, such as scopes or other instruments, to be inserted through the urinary tract. As a result, trauma to tissue and organs often results unless the urinary tract is protected. Furthermore, the insertion of a medical instrument into the kidney and bladder through the urethra and ureter can inhibit the flow of urine out of the kidney or the bladder. If the flow of urine is impeded for an extended period of time, the kidney and/or the bladder can be irreversibly damaged.

As a result, a medical practitioner must intermittently remove any medical instruments from the kidney, the urethra, and the ureter during a medical procedure. This, however, requires repeated reintroduction of the instrument, further increasing trauma to the tissue and organs. To avoid this problem, certain practitioners use an invasive kidney or bladder catheter that is inserted directly into the back of a patient to drain the respective organ. Such catheters, however, cause even more trauma and can lead to infection as well as leakage. In addition, such drainage devices also lengthen the recovery time for a patient who undergoes such a medical procedure.

SUMMARY

A medical procedure involving the insertion of standard medical devices and instruments into the urinary system interrupts the flow of urine, which can cause irreversible damage to the organs in the urinary system. The present invention mitigates the risk of damage to organs and surrounding body tissue when evaluating and/or treating the urinary system. The present invention allows for drainage of urine from the kidney and/or the bladder, while simultaneously allowing for multiple insertions and/or prolonged maintenance of a medical instrument in the urinary tract.

Generally, a medical device according to the invention includes a tubular access member and a tubular drainage member. The tubular access member allows a medical practitioner to interrogate a target organ (such as the kidney or bladder) with a medical instrument, such as a scope. The tubular drainage member allows a medical practitioner to simultaneously drain fluid from the interrogated organ (or from any other organs in the urinary system) while maintaining the tubular access member inside a patient. For example, a medical device according to the invention allows for the interrogation of a kidney with a medical instrument, while at the same time allowing for drainage from the kidney and/or the bladder.

In general, in one aspect, the invention features a medical device for accessing a cavity in a body. The medical device includes a tubular access member for insertion into a urinary tract. The tubular access member includes an insertion end, a proximal end, and a lumen. The tubular access member is adapted to allow access for at least one medical instrument through the lumen. The medical device also includes a tubular drainage member for draining fluid from an organ of a urinary system, such as the bladder and/or the kidney. The tubular drainage member includes a first end, a proximal end, and a lumen.

Embodiments according to this aspect of the invention can include the following features. The tubular drainage member can surround at least a portion of the tubular access member to define a space therebetween. The tubular access member and the tubular drainage member can be substantially concentric. Furthermore, the ends of the tubular access member and the tubular drainage member can be open. The inner circumference of the tubular drainage member can be greater than the outer circumference of the tubular access member. Furthermore, the tubular access member and/or the tubular drainage member can be slideably moveable.

Embodiments according to this aspect of the invention also can include the following other features. The tubular access member can taper inward at the insertion end. The tubular access member and/or the tubular drainage member may include a plurality of apertures for migration of fluid. The tubular drainage member can be sized such that the plurality of apertures extends from a location in the bladder to the proximal end of the tubular drainage member. The tubular drainage member also can be sized to extend from a location in the bladder to a location beyond the urethra. The first end of the tubular drainage member can extend to form a coil or, alternatively, a balloon. The tubular drainage member and the tubular access member can be the same. The tubular drainage member can include a valve.

In general, in another aspect, the invention features a medical device including a tubular access member for insertion into a urinary tract, wherein the tubular access member includes an open insertion end, an open proximal end and a lumen. The tubular access member is adapted to allow access for at least one medical instrument through the lumen. The medical device also includes a tubular drainage member for draining fluid from an organ of a urinary system, such as the bladder and/or the kidney. The tubular drainage member includes a first end, a drainage end, and a lumen.

Embodiments according to this aspect of the invention can include the following features. A portion of the tubular access member and a portion of the tubular drainage member can be coupled. The tubular drainage member can extend substantially in parallel with a portion of the tubular access member. Also, the inner circumference of the tubular access member can be greater than the inner circumference of the tubular drainage member. The tubular drainage member can extend from a location in the bladder to a location beyond the urethra. Furthermore, the tubular access member and/or the tubular drainage member can be slideably moveable.

Embodiments according to this aspect of the invention also can include the following other features. The tubular access member and/or the tubular drainage member can include a plurality of apertures for migration of fluid. The tubular drainage member can be sized such that the plurality of apertures can extend from a location in the bladder to the proximal end of the tubular drainage member. The ends of the tubular drainage member can be open. The tubular access member can taper inward at the insertion end. The first end of the tubular drainage member can extend to form a coil or, alternatively, a balloon. The tubular drainage member can include a valve.

In general, in another aspect, the invention features a method of simultaneously draining fluid from the urinary tract of a patient while maintaining access to a target organ for a medical instrument. The method includes the steps of extending a medical device through a urethra to a target organ of the urinary system. The device includes a tubular access member and a tubular drainage member. The method also includes allowing drainage of fluid into a lumen of the tubular drainage member from an organ of the urinary system while allowing access for at least one medical instrument in a lumen of the tubular access member.

Embodiments according to this aspect of the invention can include the following features. A medical instrument can reside in the lumen of the tubular access member for a period of time, such as the period of time sufficient to perform more than a single medical procedure on a patient. Methods according to this aspect of the invention can also include inserting a medical instrument into the lumen of the tubular access member. Methods according to this aspect of the invention also can include removing the medical instrument from the lumen of the tubular access member. Furthermore, methods according to this aspect of the invention also include re-inserting the medical instrument into the lumen of the tubular access member.

These and other objects, along with the advantages and features of the present invention herein disclosed, will become apparent through reference to the following description, the accompanying drawings, and the claims. Furthermore, it is to be understood that the features of the various embodiments described herein are not mutually exclusive and can exist in various combinations and permutations.

BRIEF DESCRIPTION OF THE DRAWINGS

In the drawings, like reference characters generally refer to the same parts throughout the different views. Also, the drawings are not necessarily to scale, emphasis instead being placed upon illustrating the principles of the invention. For example, the following figures show embodiments of medical devices according to the invention and the body in which the device is deployed that are not necessarily drawn to scale, but instead are intended to illustrate the principles of the invention.

FIG. 3A shows a profile view of an exemplary medical device having a tubular access member while in a body. The exemplary tubular access member has a plurality of apertures for migration of fluid, in which the apertures extend from the bladder cavity to the proximal end of the tubular access member.

FIG. 3B shows a profile view of an exemplary medical device having a tubular access member while in a body. The exemplary tubular access member has a plurality of apertures for migration of fluid, in which the apertures extend from the kidney cavity to the proximal end of the tubular access member.

FIG. 4A shows a profile view of an exemplary medical device in a body. The tubular drainage member surrounds a portion of the tubular access member that extends from the kidney cavity to the proximal end of the tubular access member. A plurality of apertures for migration of fluid is located on the tubular drainage member.

FIG. 4B shows a profile view of an exemplary medical device in a body. The tubular drainage member surrounds a portion of the tubular access member that extends from the bladder cavity to the proximal end of the tubular access member. A plurality of apertures for migration of fluid is located on the tubular drainage member.

FIG. 6A shows a profile view of an exemplary medical device in a body. This embodiment of the medical device includes a tubular drainage member that extends substantially in parallel with a portion of the tubular access member. The tubular drainage member extends from the bladder cavity to outside the body. The tubular drainage member also includes a coiled portion.

FIG. 6B shows a profile view of an exemplary medical device in a body. This embodiment of the medical device includes a tubular drainage member that extends substantially in parallel with a portion of the tubular access member. The tubular drainage member extends from the bladder cavity to outside the body and includes an inflatable balloon.

FIG. 7A shows a profile view of an exemplary medical device in a body. This embodiment of the medical device includes a tubular drainage member that extends substantially in parallel with a portion of the tubular access member. Both members extend from the kidney cavity to outside the body. The tubular drainage member also includes a plurality of apertures.

FIG. 7B shows a profile view of an exemplary medical device in a body. This embodiment of the medical device includes a tubular drainage member that extends substantially in parallel with a portion of the tubular access member. The tubular drainage member extends from the bladder cavity to outside the body. The tubular drainage member also includes a plurality of apertures.

FIG. 9 shows a profile view of an exemplary medical device having a ureteral access sheath and dilator.

DETAILED DESCRIPTION

As set forth herein, a medical device according to the invention allows a practitioner to simultaneously drain fluid from the urinary system of a patient while maintaining a medical device in the urinary tract. Generally, a medical device according to the invention includes a tubular access member and a tubular drainage member. The tubular access member allows a medical practitioner to interrogate a target organ (such as the kidney or bladder) with a medical instrument, such as a scope. The tubular drainage member allows a medical practitioner to simultaneously drain fluid from the interrogated organ (or from any other organs in the urinary system) while maintaining the tubular access member inside a patient. For example, a medical device according to the invention allows for the interrogation of a kidney with a medical instrument, while at the same time allowing for drainage from the kidney and/or the bladder. In addition, a medical practitioner can maintain the tubular access member in the patient during the whole medical procedure, and even, for a prolonged period of time after the medical procedure.

Figures 1A, 1B:
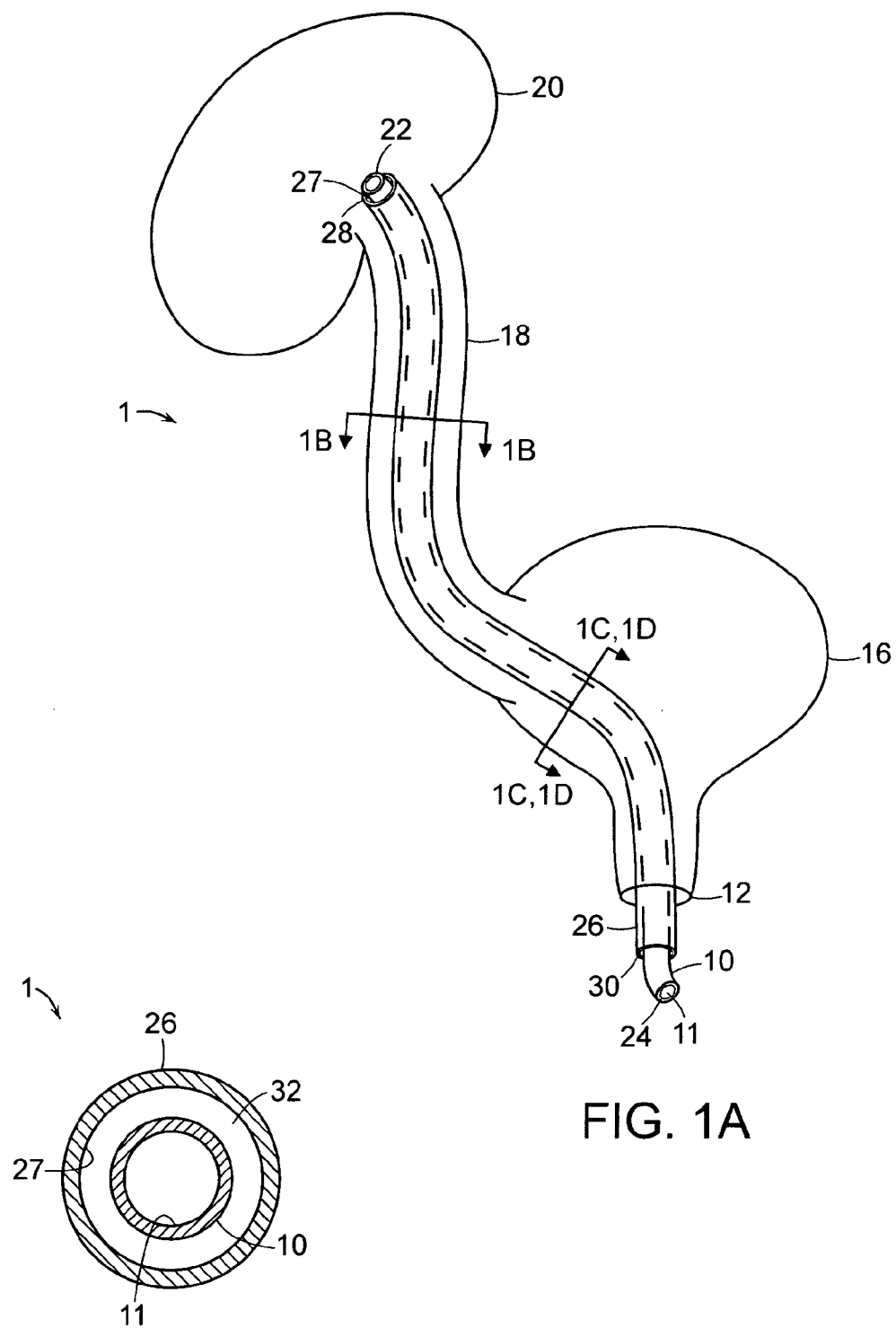
FIG. 1A shows a profile view of an exemplary medical device in a body. This embodiment of the medical device includes a drainage member that surrounds a tubular access member.
FIG. 1B shows a cross-sectional view of the exemplary medical device of FIG. 1A.

In general, all of the following embodiments of the medical device allow for drainage of fluids while simultaneously providing for the insertion and maintenance of a medical instrument through an anatomical lumen. As shown in FIG. 1A, a medical device 1 includes a tubular access member 10. The tubular access member 10 allows for insertion of a medical instrument through the urethra 12. The tubular access member 10 is extended through the urethra 12 and into the bladder 16. The tubular access member 10 also extends through the ureter 18 and into the kidney 20. The tubular access member 10 includes an insertion end 22, a proximal end 24, and a lumen 11. The tubular access member 10 is adapted to allow access of at least one medical instrument through the urethra 12 and ureter 18. The medical device also includes a tubular drainage member 26. The tubular drainage member 26 allows for draining fluid from an organ of a urinary tract, such as the bladder 16 or the kidney 20. Referring again to FIG. 1A, the tubular drainage member 26 also is designed to extend through the urethra 12 and into at least a portion of the bladder 16. In certain embodiments, the tubular drainage member can also extend through the ureter 18 and into the kidney 20 as depicted in FIG. 1A. The tubular drainage member 26 includes a first end 28, a proximal end 30, and a lumen 27.

As shown in FIG. 1A, the tubular drainage member 26 can surround a portion of the tubular access member 10 that extends from outside the body into the kidney 20. Also, as depicted in FIG. 1A, the ends of the tubular access member 10 are open in the exemplary embodiment depicted to allow for a medical instrument to enter the proximal end 24 and exit the insertion end 22. The end of the tubular drainage member 26 also can be open to allow for the entrance of fluid in the first end 28 and exit of the fluid through the proximal end 30.

Figure 1C:
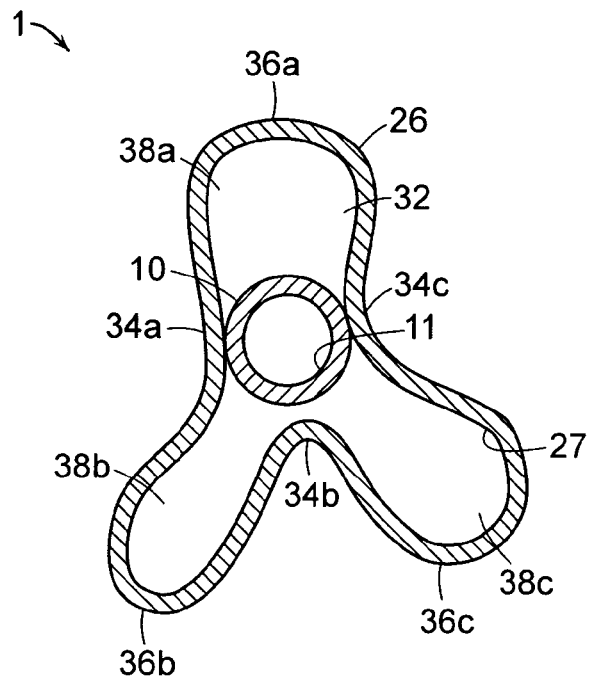
FIG. 1C shows an alternative cross-sectional view of the exemplary medical device of FIG. 1A.
Figure 1D:
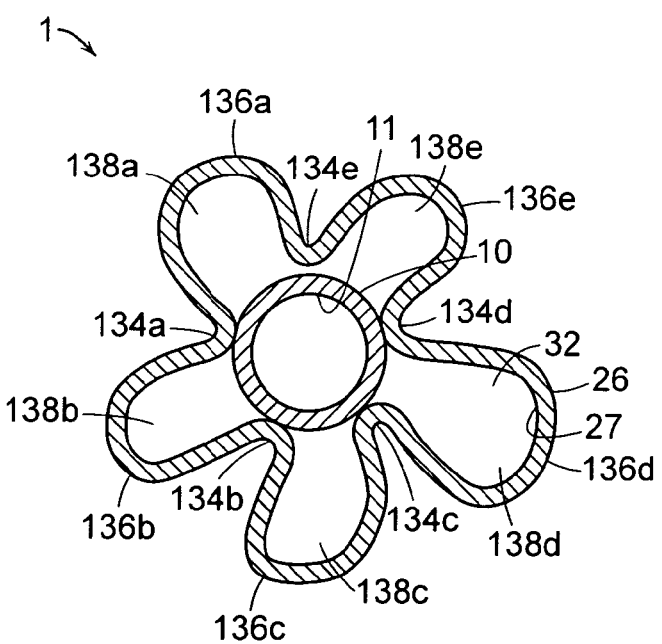
FIG. 1D shows an alternative cross-sectional view of the exemplary medical device of FIG. 1A.

FIGS. 1B-1D depict alternative cross-sections of the configuration exemplified in FIG. 1A. The tubular drainage member 26 surrounds the tubular access member 10 to define a space 32 therebetween. The actual size of the medical device is dimensioned to fit the requirement of its application in the body. The tubular drainage member 26 and the tubular access member 10 can be made from a single material or each can be made from a different material.

Referring now to FIG. 1B, in some embodiments, the tubular access member 10 and the tubular drainage member 26 are substantially concentric, thereby forming a substantially annular space 32. The inner circumference of the tubular drainage member 26 can be greater than the outer circumference of the tubular access member 10. Entry and exit of a medical instrument is accomplished through the lumen 11 of the tubular access member 10. The dimensions of the tubular drainage member 26 can be varied and/or controlled to regulate the amount and/or rate of fluid that is drained from the body. Fluid is drained from the body through the space 32, the tubular access member 10 or a combination thereof. Alternatively or additionally, a valve can be added to shut-off the flow of fluid.

Referring now to FIG. 1C, the tubular drainage member 26 features one or more external discharge channels 34a, 34b, 34c and one or more projections 36a, 36b, 36c. Optionally, at least a portion of a channel touches the tubular access member 10. A subspace 38a, 38b, 38c is defined between each projection 36a, 36b, 36c and the tubular access member 10. All or a portion of the length of the tubular drainage member 26, from the first end 28 to the second, or proximal end 30, may have the cross section of the tubular drainage member 26 shown in FIG. 1C. Fluid may drain to exit the body by, for example, passing on the external surface of the tubular drainage member 26 through one or more channels 34a, 34b, 34c.

Referring to FIGS. 1A and 1C, in one embodiment, urine is transported from the bladder 16 via the external surface of the tubular drainage member 26. The channels 34a, 34b, 34c act as external urine discharge channels to transport urine from the bladder 16 through the urethra 12 and out of the body. Optionally, portions of the tubular drainage member 26 between the bladder 20 and the ureter 18 feature the cross sectional shape shown in FIG. 1B.

Referring again to FIGS. 1A and 1C, in another embodiment, the tubular drainage member 26, which extends from outside the body into the kidney 20 and the length of the tubular drainage member 26, from the first end 28 to the second, or proximal end 30, features external drainage channels 34a, 34b, 34c. Fluid drains from the kidney 20 to exit the body by any or a combination of one or more external drainage channel 34a, 34b, 34c, the space 32, one or more subspaces 38a, 38b, 38c, and the tubular access member 10. Fluid present in the bladder 16 exits on the external surface of the tubular drainage member 26 via one or more external drainage channels 34a, 34b, 34c and drains and exits through the urethra 12 and out of the body.

FIG. 1D depicts a tubular drainage member 26 that features five external drainage channels 134a, 134b, 134c, 134d, 134e, five projections 136a, 136b, 136c, 136d, 136e and five subspaces 138a, 138b, 138c, 138d, 138e. Each subspace is defined between each projection and the tubular access member 10.

Referring to FIGS. 1A and 1D, in one embodiment, urine is transported from the bladder 16 through the urethra 12 and out of the body on the external surface of the tubular drainage member 26 via one or more external discharge channels 134a, 134b, 134c, 134d, 134e. Alternatively, fluid drains from the kidney 20 to exit the body by any or a combination of one or more external drainage channels 134a, 134b, 134c, 134d, 134e the space 32, one or more subspaces 138a, 138b, 138c, 138d, 138e, and the tubular access member 10.

The channel cross section may feature any of a variety of shapes, for example, a channel may be curved, or have any of a variety of geometric cross-sectional shapes (e.g., triangular, square, circular, and semi-circular). Similarly, the projection cross section may feature any of a variety of shapes, for example, a projection may be curved or have any of a variety of geometric cross sectional shapes (e.g., triangular, square, circular, and semicircular). The shape and number of each channel and projection may be selected to fit a particular patient and/or medical application.

The tubular members as provided herein can be manufactured from any appropriate biocompatible or medical grade material including, but not limited to, polymers, polyurethane, plastics, latex, and polyethylene. Tubular members according to the invention are preferably flexible and kink resistant. For example, tubular members according to the invention can include a reinforced coil sheath to avoid kinking or bending when inserted into an anatomical lumen. In addition, tubular members can be coated to ease insertion and/or retraction, such as with a hydrophilic coating. However, one skilled in the art understands that the principles according to the invention can be embodied in a medical device having any appropriate material or materials that is biocompatible, for example, polyurethane and silicone. In fact, in some embodiments, a medical device according to the invention can be structured and arranged, at least in part, with a shape-memory material that enables tubular members to assume a pre-determined configuration, for example, nitinol, polyanhydride and polycaprolactone.

The dimensions of the medical device 1 will vary to suit a particular application and/or patient. In one example, the tubular drainage member has an outside diameter from about 4 Fr. to about 20 Fr., preferably, about 10 Fr. to about 16 Fr. The size and/or dimensions of the tubular access member can vary, for example, based upon size and/or dimension of the tubular drainage member. In one example, the inside diameter of the tubular access member ranges from about 4 Fr. to about 16 Fr., preferably about 10 Fr. to about 14 Fr. Also, generally, the outer diameter of the tubular access member depends, in part, on the inner dimension of the tubular drainage member. For example, the difference between the outer diameter of the tubular access member and the inner diameter of the tubular drainage member can be less than about 1 Fr., about 2 Fr., about 3 Fr., about 4 Fr., or about 5 Fr. or greater. A medical device according to the invention includes a tubular access member having an outer diameter of about 7 Fr. to about 18 Fr. These dimensions are given for illustrative purposes only and are not meant to be limiting.

The overall length of the medical device 1 of the present invention depends on the application for which the medical device 1 is intended. Generally, the overall length of the medical device 1 will range from about 20 cm to about 250 cm. In one embodiment and with respect to urinary applications, the total length of the device is about 10 cm to about 100 cm, and, preferably, from about 20 cm to about 55 cm. However, the length of a medical device 1 as contemplated herein can range from below about 25 cm, to about 25 cm to 55 cm, and greater than about 55 cm. As shown herein, a tubular drainage member can have substantially the same length as the tubular access member in certain embodiments. Also, a tubular drainage member can be shorter than the tubular access member, for example, in certain embodiments where the tubular drainage member drains directly from the bladder. However, one skilled in the art understands that the medical device of the present invention can be of any appropriate length based upon the dimensions required for a particular patient or group of patients, and also based upon the organs and/or anatomical lumens sought to be evaluated. For example, devices for use on children generally will be of lesser lengths as compared to those devices intended to be used on adults. Similarly, devices for use with animals are adapted for their particular anatomies.

Figure 2:
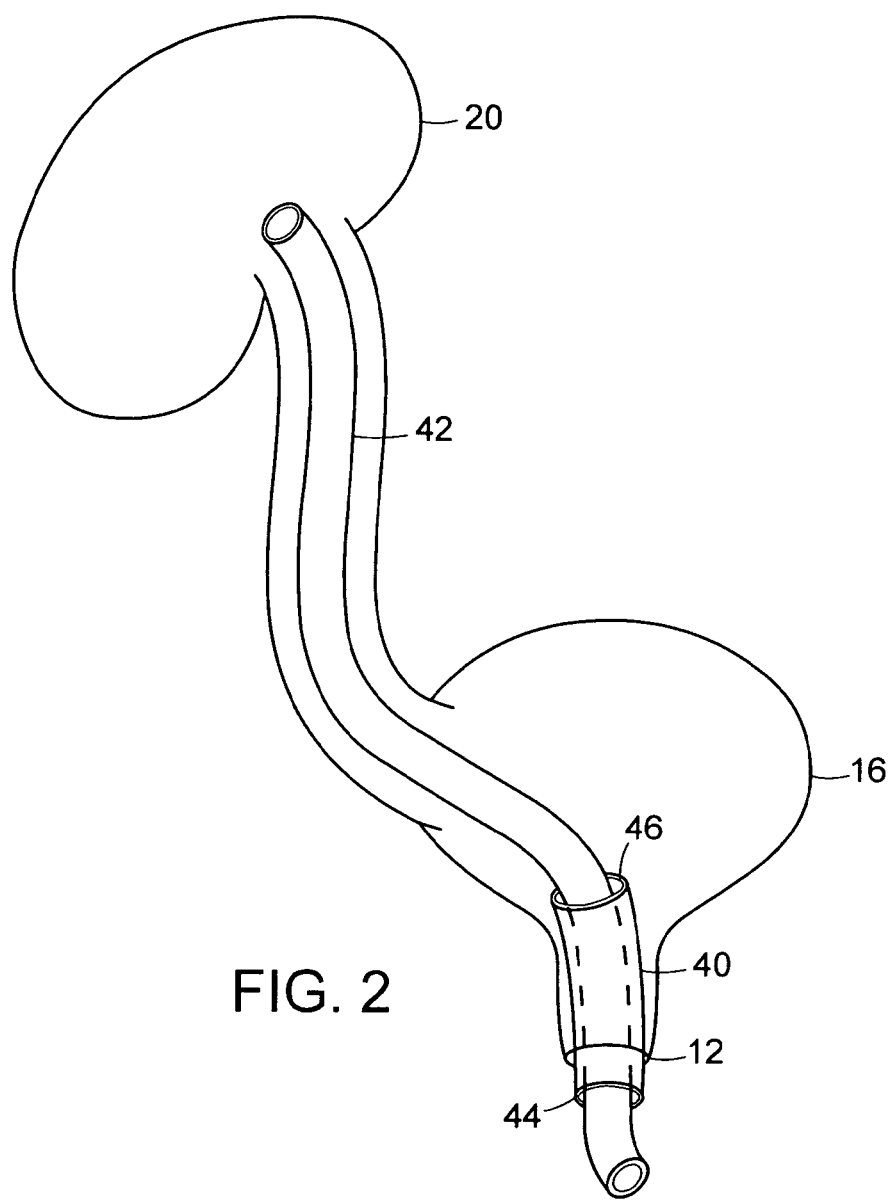
FIG. 2 shows a profile view of an exemplary medical device in a body. This embodiment of the medical device includes a drainage member that resides in the bladder and surrounds a portion of a tubular access member.

Referring to FIG. 2, a tubular drainage member 40 can be sized to extend from a location in the bladder 16 to a location extending beyond the urethra 12 and outside of the body. The ends of the tubular drainage member 40 can be open. For example, a first end 46 of the tubular drainage member 40 can be open to allow for the entrance of fluid into a space between the tubular access member 42 and the tubular drainage member 40. The fluid enters from the bladder 16 into the first end 46 of the tubular drainage member 40 and exits through the second, or proximal end 44 of the tubular drainage member 40.

The tubular drainage member 40 may feature one or more cross sectional shapes as described above with reference to FIGS. 1B-10. Referring now to FIGS. 1B-1D and FIG. 2, fluid may drain from the bladder 16 through the urethra 12 to exit the body by any or a combination of one or more external drainage channels, one or more subspaces, the space between the tubular drainage member 40 and the tubular access member 46, and the tubular access member 46 itself.

Also, in some embodiments, a tubular access member 46 according to the invention can be slideably moveable. For example, the tubular access member 46 may be slideably moveable relative to a tubular drainage member 40. Similarly, a tubular drainage member 40 can be slideably moveable so that different portions of the tubular access member 46 can be surrounded. A handle can actuate movement of the tubular access member 46 and/or the tubular drainage member 40.

Referring to FIGS. 3A and 3B, in some embodiments, a tubular access member 50 includes a plurality of apertures 52 for migration of fluid. The plurality of apertures 52 provides for effective and efficient migration of fluids from a location within the urinary tract, such as the kidney 20, bladder 12 or ureter 18, for example. The fluid migrates into the lumen of the tubular access member 50 and drains and exits through the urethra 12 and out of the body. The plurality of apertures 52 can be disposed along a portion of (see, for example, FIG. 3A) or, alternatively, along the full length of (see, for example, FIG. 3B) the tubular access member 50. Referring to FIGS. 4A and 4B, a tubular drainage member (60 and 62, respectively) can include a plurality of apertures (61 and 63, respectively) for migration of fluid. Also, as shown in FIG. 4B, apertures 63 can extend from a location in the bladder 16 to a location beyond the urethra 12 toward the second, or proximal end 64 of the tubular drainage member 62. Also, as shown in FIG. 4A, apertures 61 can extend from a location in the kidney 20 to a location beyond the urethra 12 toward the second, or proximal end 65 of the tubular drainage member 60.

Apertures 61, 63 according to the invention can assume any shape, such as, for example, circles, squares, ovals, and any other geometric or irregular shape. In fact, in some embodiments, apertures 61, 63 include slits, perforations, or any other miniature openings that allow for passage or seepage of fluids through a side of a tubular member. In a particular embodiment, the apertures 61, 63 are circles having diameters of about 1 mm to about 3 mm. The apertures 61, 63 can extend from a location in the bladder 16 to a second, or proximal end 64, 65 of the tubular drainage member 62, 60.

Figure 5A:
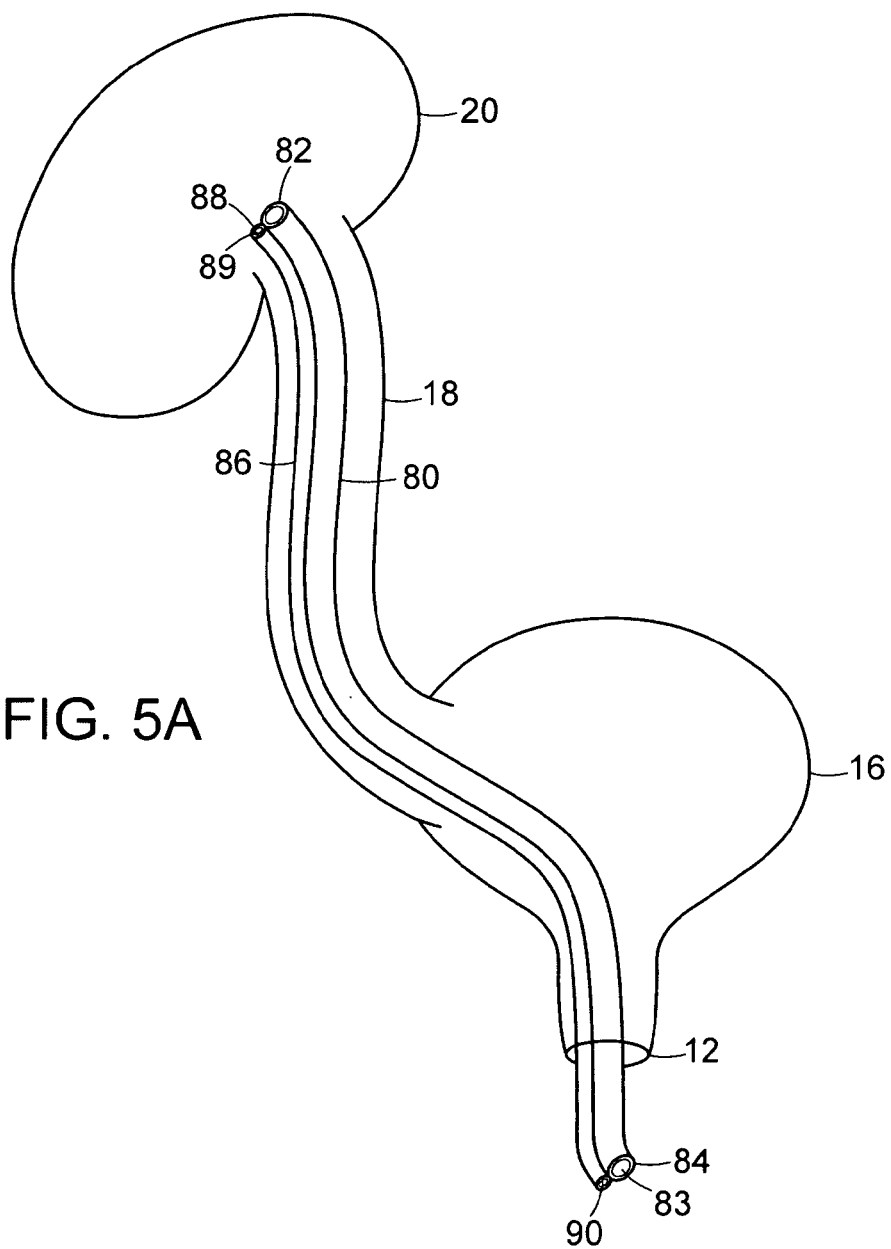
FIG. 5A shows a profile view of an exemplary medical device in a body. This embodiment of the medical device includes a tubular drainage member that extends substantially in parallel with a portion of the tubular access member. Both members extend from the kidney cavity to outside the body.

In other embodiments, the invention features a medical device 1 having a tubular drainage member 86 that extends substantially in parallel with a portion of the tubular access member 80. Referring to FIG. 5A, a medical device 1 according to the invention includes a tubular access member 80. The tubular access member 80 is adapted to allow access of at least one medical instrument through the urethra 12 and the ureter 18. Also, the tubular access member 80 includes an open insertion end 82, an open proximal end 84, and a lumen 83.

Referring again to FIG. 5A, the medical device 1 also includes a tubular drainage member 86. The tubular drainage member 86 is adapted for draining fluid from an organ of a urinary tract, such as the bladder 16 (as shown in FIGS. 6A and 6B) or the kidney 20 (as shown in FIG. 5A). The tubular drainage member 86 further includes an open first end 88, an open drainage end 90, and a lumen 89. As shown in FIG. 5A, the tubular drainage member 86 extends substantially in parallel with a portion of the tubular access member 80. Referring again to the embodiment depicted in FIG. 5A, the tubular access member 80 and the tubular drainage member 86 are designed to extend through the urethra 12 and into the bladder 16. Also, the tubular access member 80, and optionally the tubular drainage member 86, extend further through the ureter 18 and into the kidney 20.

Figure 5B:
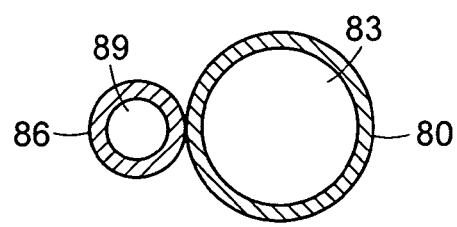
FIG. 5B shows a cross-sectional end view of the exemplary medical device of FIG. 5A.
Figure 8A:
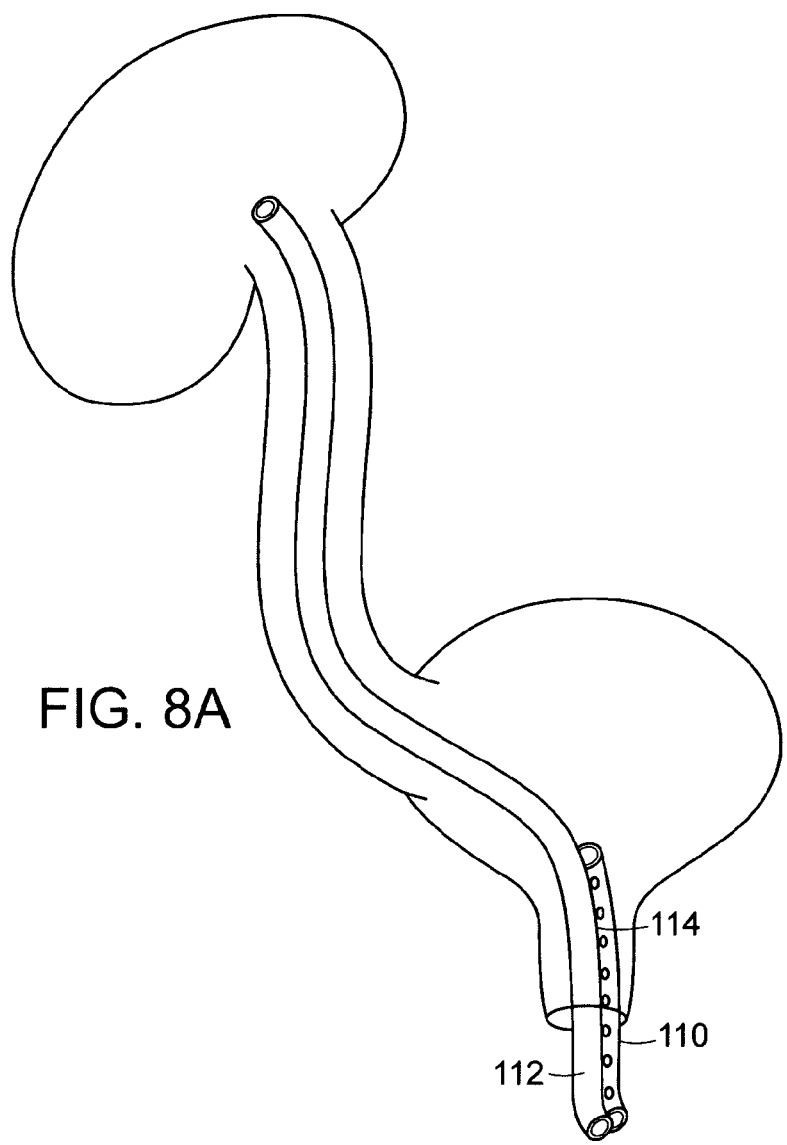
FIG. 8A shows a profile view of an exemplary medical device in a body. This embodiment of the medical device includes a tubular drainage member that extends substantially in parallel with a portion of the tubular access member. The tubular drainage member extends from the bladder cavity to outside the body. The tubular drainage member and the tubular access member share a common portion of a side of a wall of the lumen. The tubular drainage member also includes a plurality of apertures.
Figure 8B:
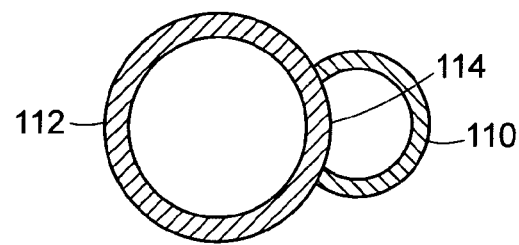
FIG. 8B shows a cross-sectional end view of the exemplary medical device of FIG. 8A.

Referring to the cross-section illustrated in FIG. 5B, the tubular drainage member 86 of FIG. 5A extends substantially in parallel with a portion of the tubular access member 80. The size of the medical device 1 is dimensioned to fit the requirement of its application in the body. The tubular drainage member 86 and the tubular access member 80 may be made from a single material or each can be made from a different material. Again referring to FIG. 5B, in some embodiments, a portion of the tubular access member 80 and a portion of the tubular drainage member 86 can be coupled. Also, the inner circumference of the tubular access member 80 can be greater than the inner circumference of the tubular drainage member 86.

Referring to the exemplary embodiment depicted in FIG. 6A, a tubular drainage member 92 can extend from a location in the bladder 16 to a location extending beyond the urethra 12 and outside of the body. The ends 94, 96 of the tubular drainage member 92 can be open. For example, an open first end 94 of the tubular drainage member 92 is open to allow for the entrance of fluid into the lumen 98 of tubular drainage member 92. The fluid enters from the bladder 16 and into the open first end 94 of the tubular drainage member 92. The fluid then exits through the open drainage end 96 and out of the body, or through a closable valve 97.

Either or both of the tubular members also can include a plurality of apertures for migration of fluid. As discussed herein and referring, for example, to FIG. 7A, apertures provide for effective and efficient drainage of fluid from a location within the urinary tract, such as the kidney 20, bladder 16, or ureter 18, for example. Fluid is drained through the urethra 12 and out of the body. Referring to FIGS. 7A and 7B, a tubular drainage member (101 and 102, respectively) includes a plurality of apertures (104 and 106, respectively) for migration of fluid. The apertures 104, 106 allow for the drainage of fluid that migrated from the body into the lumen of a tubular drainage member 101, 102. Also, as shown in FIG. 7B, apertures 104, 106 can extend from a location in the bladder 16 to a location beyond the urethra 12 toward an open drainage end 108 of the tubular drainage member 102. The tubular members according to the present invention can have a variety of configurations. For example, a first end 94 of a tubular drainage member 92 can extend to form a coil 99 (see FIG. 6A). A coil configuration 99 provides for a greater surface area to attract and drain fluids. In addition, a coil configuration 99 can help maintain the respective tubular member in place within the body organ. Also, in some embodiments, the drainage member 92 of the medical device 1 can include a balloon 100, such as that associated with well-known Foley catheters (see FIG. 6B). Such a structure aids in securing the tubular drainage member's 92 placement in the bladder 16 so it can effectively drain urine from the bladder 16 as well as secure the tubular access member 80 in place during insertion and removal of a medical instrument. Furthermore, a first end 94 of a tubular drainage member 92 can taper inward at the first end 94. Similarly, a tubular access member 80 can taper inward at the insertion end 82. A tapered end 82 generally provides less trauma to the affected tissue and/or organ. In addition, referring to FIGS. 5A and 88, a drainage tubular member 110 can share a common portion 114 of a side (or portion of the circumference) with a tubular access member 112.

Also, in some other embodiments having a parallel design, the tubular access member is slideably moveable relative to the tubular drainage member. However, in some embodiments, the tubular drainage member is slideably moveable relative to the tubular access member. A handle can actuate movement of the tubular access member and/or the tubular drainage member.

Medical devices according to the present invention can also accept guidewires. For example, guidewires ranging from about 0.035 inches to about 0.038 inches can be used with the tubular members of the invention. Some embodiments of the invention can also accept guidewires less than about 0.035 inches and greater than about 0.038 inches.

In general, in another aspect, the invention provides a method of simultaneously draining fluid from the urinary tract of a patient while maintaining a medical instrument, e.g., an imaging scope, a retrieval device, and the like, in the urinary system of a patient. Referring, for example, to FIG. 5A, the method includes extending a medical device 1 comprising a tubular access member 80 for insertion through a urethra 12 and a ureter 18 and a tubular drainage member 86 for draining fluid from an organ of a urinary system, such as a bladder 16 or a kidney 20. For example, a medical practitioner extends a medical device through the urethra 12 and ureter 18 to a target organ of the urinary system. The tubular access member 80 is adapted to provide access for at least one medical instrument through the urethra 12 and the ureter 18. The tubular drainage member 86 extends substantially in parallel with a portion of the tubular access member 80. FIG. 5A shows a tubular drainage member 86 substantially in parallel with a tubular access member 80 from the kidney 20 to a location beyond the urethra 12 and the ureter 18. FIG. 6A shows a tubular drainage member 92 substantially in parallel with a tubular access member 80 from the bladder 16 to a location beyond the urethra 12. Furthermore, the medical practitioner allows drainage of fluid into a lumen 98 of the tubular drainage member 92 from an organ of the urinary system while maintaining the medical instrument in a lumen 83 of the tubular access member 80. Referring again to FIG. 5A, a medical practitioner thereafter can insert a medical instrument through a lumen 83 of the tubular access member 80 and through the urethra 12, and into the bladder 16. The medical practitioner can also extend the medical instrument through the lumen 83 of the tubular access member 80, further through the ureter 18, and into the kidney 20.

A medical device according to the present invention can include tubular members comprising a polymeric material made of polytetrafluoroethylene (PTFE), expanded polytetrafluoroethylene (EPTFE), ethylene tetrafloroethylene (ETFE) or other suitable material that exhibits laser resistant characteristics (e.g., light color) that prevents or minimizes damage to the tubular members or other elements of the medical device during a medical procedure. In one embodiment, the color of the tubular access member differs from the color of the tubular drainage member and from the color of other elements of the device (e.g., the tubular access member is a light color) in order to assist a medical practitioner in determining the location of the respective member during a medical procedure. In addition, a tubular member of the present invention can include radiopaque markers to facilitate the medical practitioner in determining the location of any of the elements of the present invention.

In practice, the tubular access member of the present invention is a type of ureteral access sheath adapted and improved to provide drainage capabilities heretofore unavailable. Thus, a practitioner can employ the tubular access member in any manner heretofore accommodated by a standard ureteral access sheath. It is understood that all the features and/or properties described herein below as characteristic of a ureteral access sheath can also be characteristic of the tubular access member of the present invention. In fact, in certain embodiments contemplated herein, the tubular access member is a ureteral access sheath and can be used accordingly.

Typically, a ureteral access sheath can be used by medical practitioners performing evaluations of a patient's urinary tract, such as performing a flexible ureteroscopy. In some embodiments of a ureteral sheath, the ureteral sheath 200 includes a lumen through which a tubular dilator 202 can pass if desired (see FIG. 9).

In some embodiments, the ureteral sheath is kink-resistant. For example, the ureteral sheath 200 can include a reinforced coil sheath 200 to avoid kinking or bending when inserted into an anatomical lumen. Furthermore, the ureteral sheath 200 can be radiopaque and can include, for example, a highly radiopaque ring at the distal tip 204 of the ureteral sheath 200. Also, the ureteral sheath 200 can have a coating that reduces friction when inserted into an anatomical lumen, thereby reducing resistance and trauma to the affected area. A ureteral sheath 200 can also accept guidewires. For example, guidewires ranging from about 0.035 inches to about 0.038 inches can be used with a ureteral sheath 200 to place the sheath 200 at a target site in the urinary system.

Dimensions of a ureteral sheath 200 of the present invention vary based upon the components for which the sheath 200 is configured to pass therein. Generally, dimensions of a ureteral access sheath 200 include an inner diameter of preferably less than about 10 Fr., more preferably from about 10 Fr. to about 16 Fr., or in some embodiments preferably greater than about 16 Fr. Also, the length of a ureteral access sheath 200 can range from preferably below about 25 cm, more preferably to about 25 cm to about 55 cm, and in some embodiments preferably greater than about 55 cm.

Figure 10A:
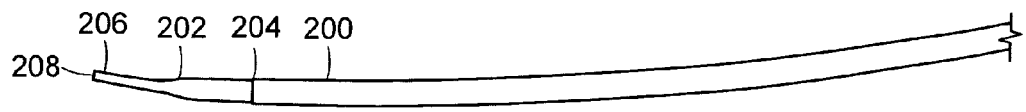
FIGS. 10A and 10B show schematic views of an exemplary medical device having a ureteral access sheath and dilator.
Figure 10B:
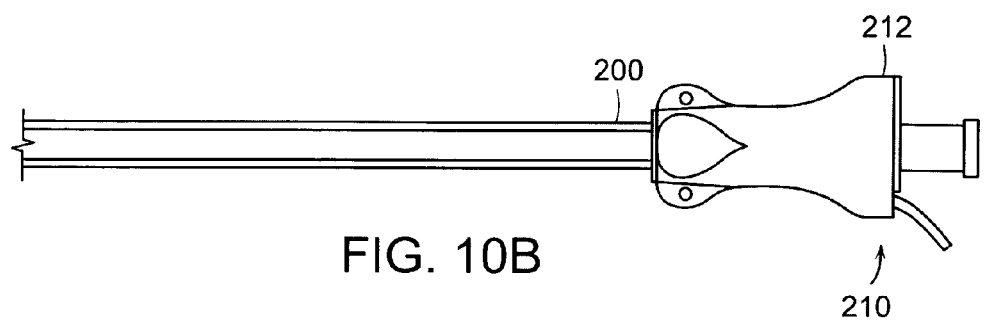

A ureteral access sheath 200 also can be compatible with other components that a medical practitioner may desire to insert into an anatomical lumen or cavity. Referring now to FIGS. 9, 10A and 10B, for example, the ureteral sheath 200 can include a lumen through which a dilator 202 can pass. In some embodiments, a dilator 202 can have an atraumatic tapered tip 208. In some embodiments, a dilator 202 and the ureteral sheath 200 may have short dual tapered tips for reducing trauma to the affected area. Also, in some embodiments, an insertion end 204 of the ureteral sheath 200 and a first end 206 of the dilator 202 can have a short distance or transition that allows for closer proximation to a target lumen.

Figure 11A:
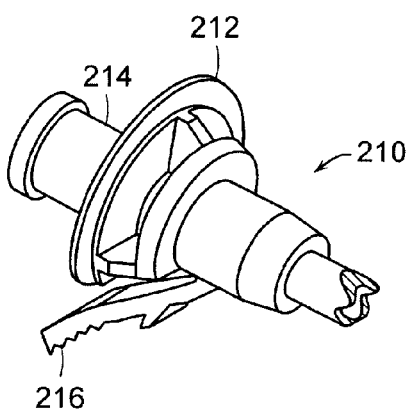
FIGS. 11A and 11B, respectively, show a perspective view and an end view of an exemplary luer lock mechanism of a medical device having a ureteral access sheath and dilator.
Figure 11B:
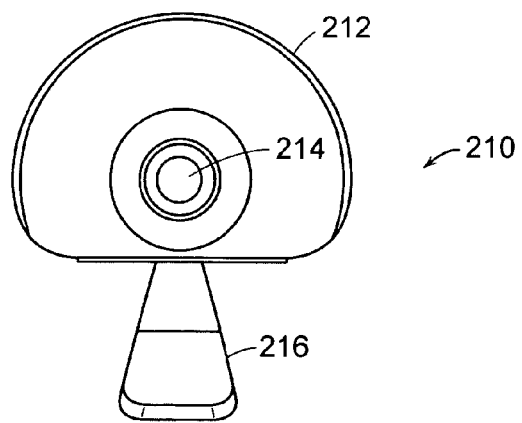

Referring to FIGS. 9, 10A, 10B, 11A, and 11B, a ureteral sheath 200 can also have a locking mechanism 210 between a dilator 202 and the sheath 200 that allows for quick opening and/or locking. A locking mechanism can have a hub design as shown in FIGS. 11A and 11B, for example. Dimensions of dilators, for example, include a dilator preferably having an outer diameter of less than about 10 Fr., more preferably about 10 to about 14 Fr., or in some embodiments preferably greater than about 14 Fr. Generally, the dimensions of a dilator (and any other components that pass inside the lumen of a ureteral access sheath) can depend on the dimensions of the ureteral access sheath and the dimensions of the target anatomical lumen.

Referring to FIGS. 10A, 10B, 11A and 11B, in operation, a medical practitioner places a dilator 202 and the ureteral access sheath 200 into a container of saline or sterile water to activate the hydrophilic coating prior to use. Thereafter, a medical practitioner places a guidewire into the desired location within the urinary system. Next, the medical practitioner inserts the dilator 202 fully inside the ureteral access sheath 200 and secures the dilator 202 by pushing the dilator 202 until it snaps into the sheath hub 212. Afterwards, the medical practitioner advances the dilator 202/sheath 200 assembly over the guidewire to the desired location. Once positioned, the medical practitioner withdraws the dilator 202 by grasping the luer 214 and the tab 216, while maintaining the ureteral access sheath's position. If desired, the tubular sheath 200 can be secured to the surgical drapes by attaching sutures through the holes located on the sheath hub 212 body. Also, the medical practitioner can introduce or insert a medical instrument or instruments through the ureteral access sheath 200 as appropriate. Also, to perform a retrograde pyelogram, the medical practitioner can insert a dilator 202 having a lumen into the ureteral access sheath 200 and inject contrast through the luer fitting 214 of the dilator 202 which is in fluid communication with the lumen of the dilator 202.

Upon completion of the access procedure, the medical practitioner can withdraw the medical device if desired. Such a ureteral access sheath having the characteristics and uses described above can be modified to include a configuration with an access tube member and drainage tube member such that access and drainage from the kidney and bladder can be accomplished simultaneously.

Having described certain embodiments of the invention, it will be apparent to those of ordinary skill in the art that other embodiments incorporating the concepts disclosed herein may be used without departing from the spirit and scope of the invention. The described embodiments are to be considered in all respects as only illustrative and not restrictive.

What is claimed is:

1. A medical device comprising:
a tubular access member for insertion into a urinary system comprising an open insertion end, an open proximal end, and a lumen, wherein the tubular access member is adapted to allow access for at least one medical instrument through the lumen, the tubular access member being sized to extend from a location in a kidney of a patient to a location beyond a urethra of the patient; and
a tubular drainage member comprising a first end portion, a drainage end portion, and a lumen for draining fluid from the urinary system, the first end portion of the tubular drainage member includes a curved portion, the open insertion end of the tubular access member being disposed apart from the first end portion of the tubular drainage member, the open proximal end of the tubular access member being disposed apart from the drainage end portion of the tubular drainage member, the tubular drainage member being sized to extend from a location in a bladder of the patient to a location beyond the urethra of the patient,
wherein a portion of the tubular access member is coupled to a portion of the tubular drainage member.

2. The medical device of claim 1, wherein the curved portion of the tubular drainage member forms a coil.

3. The medical device of claim 1, wherein at least one of the tubular access member and the tubular drainage member includes a plurality of apertures for migration of fluid.

4. The medical device of claim 1, wherein the tubular access member tapers inward at the insertion end.

5. The medical device of claim 1, wherein the tubular drainage member is sized to extend from a location in the urinary system to a location beyond the urethra.

6. The medical device of claim 1, wherein the tubular drainage member includes a valve.

7. The medical device of claim 1, wherein the tubular access member includes medial portion disposed between the open insertion end and the open proximal end, the tubular drainage member includes a middle portion disposed between the first end portion and the drainage end portion, the medial portion of the tubular access member being coupled to the middle portion of the tubular drainage member.

8. The medical device of claim 1, wherein the tubular drainage member includes a securement member disposed between a middle portion of the tubular drainage member and the first end portion of the tubular drainage member.

9. The medical device of claim 1, wherein the tubular access member includes medial portion disposed between the open insertion end and the open proximal end, the tubular drainage member includes a middle portion disposed between the first end portion and the drainage end portion, the medial portion of the tubular access member being coupled to the middle portion of the tubular drainage member, the tubular drainage member includes a securement member disposed between the middle portion of the tubular drainage member and the first end portion of the tubular drainage member.

10. The medical device of claim 1, wherein the tubular drainage member is disposed outside the lumen of the tubular access member.

11. A medical device comprising:
a tubular access member for insertion into a urinary system having an open insertion end, an open proximal end, a medial portion disposed between the open insertion end and the open proximal end, and a lumen, wherein the tubular access member is adapted to allow access for at least one medical instrument through the lumen, the tubular access member being sized to extend from a location in a kidney of a patient to a location beyond a urethra of the patient; and
a tubular drainage member having a first end portion, a drainage end portion, a middle portion disposed between the first end portion and the drainage end portion, and a lumen for draining fluid from the urinary system, the middle portion of the tubular drainage member being coupled to the medial portion of the tubular access member, the open insertion end of the tubular access member being disposed apart from the first end portion of the tubular drainage member, the open proximal end of the tubular access member being disposed apart from the drainage end portion of the tubular drainage member, the tubular drainage member being sized to extend from a location in a bladder of the patient to a location beyond the urethra of the patient.

12. The medical device of claim 11, wherein the tubular drainage member includes a portion that forms a coil.

13. The medical device of claim 11, wherein at least one of the tubular access member and the tubular drainage member includes a plurality of apertures for migration of fluid.

14. The medical device of claim 11, wherein the tubular access member tapers inward at the insertion end.

15. The medical device of claim 11, wherein the tubular drainage member is sized to extend from a location in the urinary system to a location beyond the urethra.

16. The medical device of claim 11, wherein the tubular drainage member includes a valve.

17. The medical device of claim 11, wherein the tubular drainage member includes a securement member disposed between the middle portion of the tubular drainage member and the first end portion of the tubular drainage member.

18. A medical device comprising:
a tubular access member for insertion into a urinary system having an open insertion end, an open proximal end, a medial portion disposed between the open insertion end and the open proximal end, and a lumen, wherein the tubular access member is adapted to allow access for at least one medical instrument through the lumen;
a tubular drainage member having a first end portion, a drainage end portion, a middle portion disposed between the first end portion and the drainage end portion, and a lumen for draining fluid from the urinary system, the middle portion of the tubular drainage member being coupled to the medial portion of the tubular access member, the open insertion end of the tubular access member being disposed apart from the first end portion of the tubular drainage member, the open proximal end of the tubular access member being disposed apart from the drainage end portion of the tubular drainage member; and
a securement member coupled to the tubular drainage member at a location on the tubular drainage member, the location on the tubular drainage member being disposed a distance from the tubular access member.

19. The medical device of claim 18, wherein an outer surface of the securement member is disposed between the tubular access member and the tubular drainage member.

* * * * *